(12) United States Patent
Norton (10) Patent No.: US 7,905,850 B2
(45) Date of Patent: Mar. 15, 2011

(54) DEVICE AND METHOD FOR COMBINING AN ATHLETIC SHOE AND CONVENTIONAL ANKLE BRACE TO LIMIT ACTIVE ANKLE INVERSION

(76) Inventor: David Norton, Carp Lake, MI (US)

( * ) Notice: Subject to any disclaimer, the term of this patent is extended or adjusted under 35 U.S.C. 154(b) by 314 days.

(21) Appl. No.: 12/221,965

(22) Filed: Aug. 8, 2008

(65) Prior Publication Data

US 2010/0036304 A1 Feb. 11, 2010

(51) Int. Cl.
*A61F 5/00* (2006.01)
(52) U.S. Cl. .......................... 602/23; 602/27
(58) Field of Classification Search ............. 602/60–64, 602/75, 22–28; 128/882
See application file for complete search history.

(56) References Cited

U.S. PATENT DOCUMENTS

| 4,547,981 A | 10/1985 | Thais et al. |
| 4,556,054 A | 12/1985 | Paulseth |
| 4,577,419 A | 3/1986 | Chassaing |
| 4,922,630 A * | 5/1990 | Robinson ........................... 36/89 |
| 5,069,202 A | 12/1991 | Prock |
| 5,090,404 A * | 2/1992 | Kallassy ........................... 602/65 |
| 5,672,156 A | 9/1997 | Jimenez Ramos |
| D385,102 S | 10/1997 | Avar |
| 5,771,608 A * | 6/1998 | Peterson ........................... 36/89 |
| 5,792,087 A | 8/1998 | Pringle |
| 5,795,316 A * | 8/1998 | Gaylord ........................... 602/27 |
| 6,056,713 A * | 5/2000 | Hayashi ........................... 602/27 |
| 6,126,625 A | 10/2000 | Lundberg |
| 6,503,218 B1 | 1/2003 | Ascheman |
| 7,497,839 B2 * | 3/2009 | Quinn et al. ..................... 602/23 |

* cited by examiner

*Primary Examiner* — Michael A. Brown
(74) *Attorney, Agent, or Firm* — Douglas S. Bishop (57) ABSTRACT

A device and method is provided wherein a non-extendable strap is attached to the interior of an athletic, or other type of shoe, commencing on the instep side, extending below the user's foot, and ankle, which has been previously fitted with a commercial brace or wrap or taped, which is inserted within the shoe, and the strap is attached within the shoe again on the outstep upper side. The strap element is drawn tight about the user's ankle when the shoe is laced, strapped, or otherwise secured about the user's foot. The strap element extends above the user's ankle, and is pulled taut and affixed to the brace, or wrap, or separately taped, at a position on the outside of the user's lower leg. The device and method of attachment allows the shoe and brace or wrap to act together, as an integrated system, to limit active ankle inversion.

22 Claims, 6 Drawing Sheets

DEVICE AND METHOD FOR COMBINING AN ATHLETIC SHOE AND CONVENTIONAL ANKLE BRACE TO LIMIT ACTIVE ANKLE INVERSION

BACKGROUND OF THE INVENTION

Ankle injuries, particularly those to supporting ligaments, have been found to be some of the most substantial lost time injuries in competitive sports. At least one study has found that such ankle injuries are the number one lost time injury in competitive sports. It has been estimated that over 83% of ankle sprains among British soccer players required more than one month's loss of competition. Other studies have shown, among basketball players, that more than 90% have histories of ankle sprains with 76% suffering recurrent sprains. A 2000 study by, Richard, Schulties & Saret, found that 20% to 50% of injuries in sports involving running and jumping are ankle injuries. Ankle injuries can also occur in non-competitive exercise, in the home, and in the work place, on a day to day basis.

Previous attempts to prevent or minimize ankle injuries have included the utilization of high top and tightly laced athletic, or other types of shoes, as well as taping, and the utilization of commercially available ankle brace devices.

Examples of external straps include U.S. Pat. No. 7,267,656, to Cooper, for an Ankle Brace capable of being worn with conventional footwear; U.S. Pat. No. 7,252,647, to Hely, for a Self-Tightening Ankle Brace; U.S. Pat. No. 6,929,617, to McCormick et al, for a Non-Bulky Ankle Brace for use with Footwear; U.S. Pat. No. 6,056,713, to Hayashi, for a Moldable Custom Fitted Ankle Brace; U.S. Pat. No. 5,843,010, to Bodmer, for a Heal and Ankle Appliance; U.S. Pat. No. 5,090,404, to Kallassy, for a Universal Ankle Support; U.S. Pat. No. 5,038,762, to Hess et al, for an Ankle Joint Orthosis; U.S. Pat. No. 5,014,691, to Cueman et al, for an Ankle Brace with Densified Batting, including a means for securing the brace to the ankle, such as Velcro® closures; as well as U.S. Pat. No. 4,875,476, to Garcia, for an Ankle Support Bandage for Prevention of Ankle Injury.

Additionally, the prior art discloses attempts by inventors to provide footwear with strap or brace elements incorporated within an athletic shoe itself, to prevent ankle injury. See, for example, U.S. Pat. No. 5,771,608, to Peterson, for a Shoe with Ankle Strap Protector; U.S. Pat. No. 5,226,875, to Johnson, for an invention captioned Athletic Footwear with Integral Ankle Support, which includes a pair of resilient braces attached to the sole interlining and calf support collar of an athletic shoe; and U.S. Pat. No. 4,922,630, to Robinson, for an Athletic Shoe with Inversion Resisting Device, including a light engaging strap disposed only on the lateral side of the shoe upper.

U.S. Pat. No. 5,672,156, to Jimenez Ramos, for a device to avoid twists in ankles, provides an independent removable device, attached directly to the leg above the ankle and to the external side of footwear.

One of the significant factors regarding athletic injuries and athletic shoes, involves the tendency, particularly for "inversion" ankle injuries, of the ankle and foot to turn or move within the shoe and to allow the shoe's sole to act as a fulcrum, increasing the inversion pressure on the ankle, leading to serious injury. This "fulcrum" function may also exist in non-athletic situations, and in circumstances where the ankle must be restrained post-injury for therapeutic purposes, whether or not the injury originated athletically. Separate ankle wraps do not address this problem, when the foot and ankle of the user is still allowed to move within the footgear. Likewise, ankle wrapping devices, when the wrapped and/or restrained ankle is inserted into footgear, even with separate tightening devices for the footgear, do not prevent this inversion injury causing movement. Strapping devices affixed only to the exterior or interior of a user's shoe do not address the movement of the foot within the footwear, nor do they alleviate potential of a shoe upper to stretch, or otherwise allow movement. Further, known shoe devices, without a separate ankle wrap, or tape, attached thereto, fail to provide the degree of support for the joints and ligaments of the ankle during movement, even if the particular shoe may be somewhat stabilized by use of strapping devices contained within it.

Thus, a need exists for a device, and method of affixation thereof, for use in athletic competition, day to day non-athletic use, and therapeutic use, which will provide the support of a direct taping or brace system for the ankle, as well as incorporate the same, by attachment, to shoes of all types, including, but not limited to, an athletic shoe, to provide an integrated brace and shoe system, which will inhibit inverted movement of the ankle within the shoe, and prevent the shoe itself from acting as a fulcrum for such invertive stress on the ankle.

Further, a need exists, for a device and method which would allow the benefits of the current invention in combination with any manufactured athletic shoe or other types of shoe and any otherwise available commercial brace or ankle wrap.

The current invention addresses a significant need in the manner set forth in the brief Summary, Drawings and Detailed Description of the Invention and method which follow.

SUMMARY OF THE INVENTION

The present invention is directed to the provision of a device and method to be utilized with a shoe, separately, or together with an ankle brace device, to prevent inversion stress on a user's ankle. The invention is intended to, and does have, both preventative and therapeutic value. It may be utilized with an athletic shoe to prevent injuries caused by excessive inversion of a user's ankle in competition, or in training, and it may be used with any type of shoe for therapeutic purposes, when an injury exists, or a user, for various medical or other health reasons, has a condition which will be aggravated by inversion of the ankle.

Most specifically, the present invention is directed to the provision of a strapping device which may be permanently, or removably, affixed within a shoe, and then attached, either separately to a user's upper leg, above the ankle, on the lateral side of the leg and ankle, or at such point, to an ankle brace already affixed about the user's ankle and leg.

In its simplest embodiment, the invention is a unitary, non extendable, flat strap. The attachment is to the shoe's interior upper and the strap device then extends upward, on the lateral side of the foot and ankle along the lateral side of the user's leg. The strap is then drawn taut and attached in taut position to the user's leg by adhesive tape or other strap or wrapping device. If the device is being utilized in conjunction with an ankle brace, the attachment may be to the ankle brace itself in such taut fashion.

In a further feature of the invention, the strap device is first attached within the shoe's upper at a point on the interior or medial side of the foot, at or below the ankle joint. The strap then extends next to the shoe's upper to the sole of the shoe, across the sole of the shoe, beneath the user's foot, and is again attached to the wall of the upper, as the strap extends upward, on the lateral, or outstep, side of the shoe's upper.

When the shoe is tightly enclosed around the user's foot, by means of the standard enclosing features of the shoe, which may be strap and buckle, laces, or any other manner in which shoes are normally secured, the strap element is adjacent to, and conforms to, the dimensions of the user's foot, beneath the ankle, between the medial and lateral sides.

In practice, the strap may be attached at the desired number of positions on the interior of the shoe's upper by being permanently sewn, by snaps, by Velcro® attachment, glue, or other like or similar fastening means.

A further significant feature of the invention is that it is particularly useful in conjunction with a device which separately limits movement of the ankle. Such device could include standard taping of the ankle with adhesive tape, or utilization of bracing devices, such as commercially available brace devices, which lace, strap or are otherwise bound around the user's ankle.

To the extent that the brace device is of a type which extends above the user's ankle around the lower leg, and, correspondingly, above the upper edge of the shoe upper element, the extending end of the strap device is then attached, by tape, snaps, straps, elastic band or strap, or other like or similar means, to the brace device itself.

In a further feature of the invention, it is possible to utilize the combination of a shoe, ankle brace device, and the strap device, wherein the ankle is enclosed both by the shoe and the brace device, and the strap device is attached by one or more of the stated means, at a point above the top of the ankle brace device. It is a further feature of the invention that the device, when attached to the shoe, for optimal prevention of ankle inversion, the strap is drawn taut, upwardly from the user's foot, and attached, in such taut position, to either the ankle brace device or the user's leg. The degree of tautness may be varied depending upon the degree to which inversion is desired to be prevented.

In a further feature of the invention, the strap element, for comfort purposes, may run from the medial side of the shoe's upper to the lateral side of the shoe's upper, beneath an insole inserted between the base of the user's foot and the primary sole of the shoe.

It is a further feature of the invention, that the strap element, which is the primary feature of the invention, used in conjunction with a shoe, either standard or athletic, and with or without a separate brace, may be utilized as a separate addition, or "kit," to add to existing footwear. As such, the strap may be removably attached to the interior walls of the shoe's upper by removable methods, including, but not limited to, hook and loop fasteners, such as Velcro®, such that one strap element could be separately utilized with more than one shoe.

It is an important feature of the invention that the strap element, with the desired method of attachment, may be utilized as a system, as a method for preventing ankle inversion, where the strap element, as described, is utilized together with a standard shoe. An ankle brace device, or ankle tape application, is placed around the user's ankle and lower leg immediately above it; the device is attached, as stated, within the shoe. The user's foot corresponding to the particular shoe is inserted within the shoe, and the laces, or straps which are used to tightly enclose the shoe around the foot, are secured. The upwardly extending portion of the strap is then drawn taut, while everting the ankle as desired, and attached to the brace, or the user's lower leg, above the shoe upper. When so placed, as previously stated, upward pressure is exerted on the strap so that the strap, when affixed, is taut. The invention is more fully described and understood by reference to the drawings and detailed description which follow.

DETAILED DESCRIPTION

Figure 7:
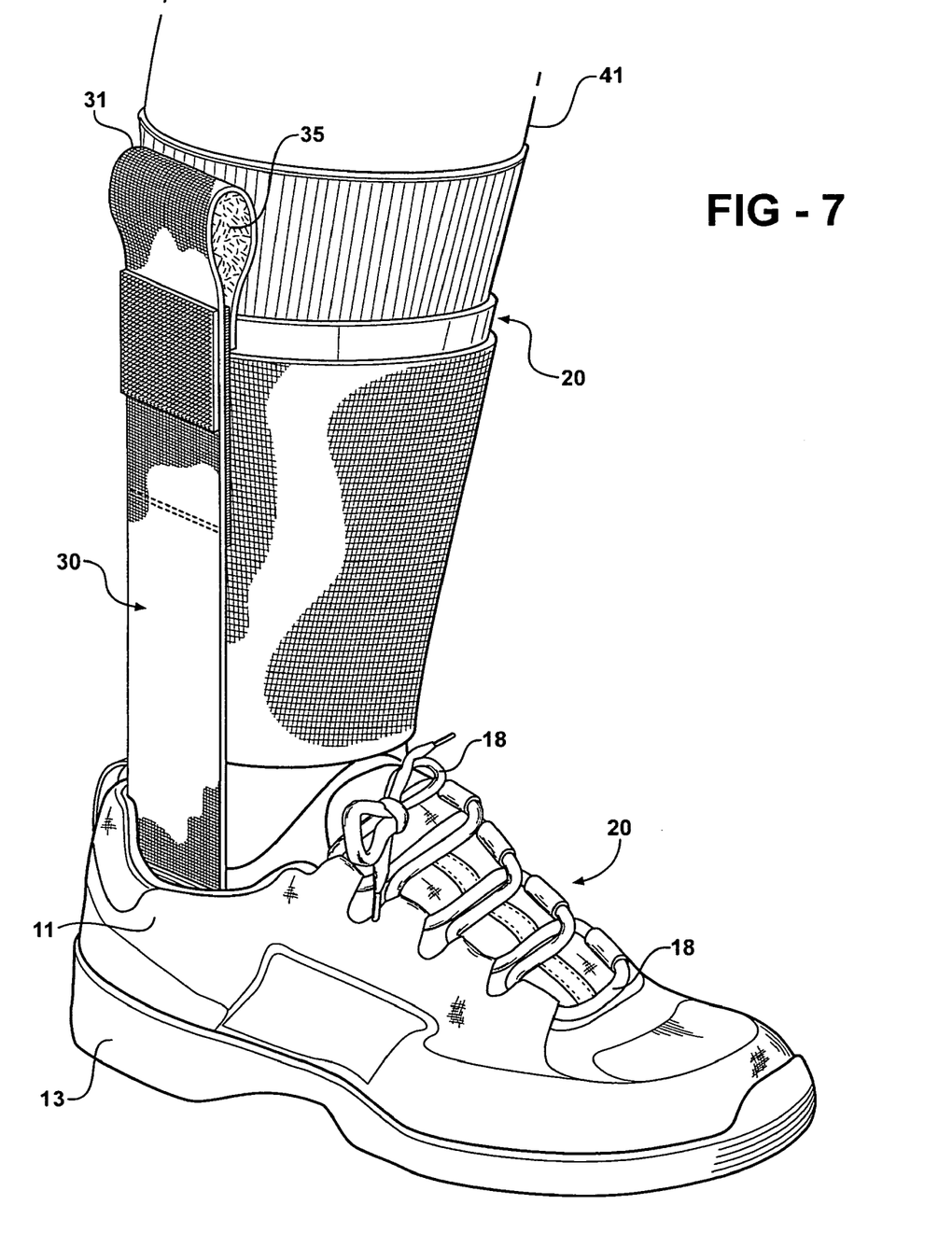
FIG. 7 is a perspective view from the lateral or outstep side of a user's right foot, with the device in place, affixed within a shoe upper and affixed above the user's ankle to the lateral or outstep side of the user's leg, with tied laces enclosing the shoe upper about the user's foot.

The invention Device and Method for Combining an Athletic Shoe And Conventional Ankle Brace to Limit Active Ankle Inversion is utilized in conjunction with a shoe 10 and an ankle brace or wrap 20. Broadly considered, the device comprises a unitary, non-extendable strap element 30. Said strap 30 is generally flat, and belt-like, and conformable to a person's foot 40 and corresponding leg 41. Said strap element 30 has a first end 31 and a second end 32. It has a defined length A which is the lineal distance between first end 31 and second end 32. Strap element 30 is used with shoe 10 having an upper portion 11, said upper 11 having an interior or inner surface 12, and a sole 13, with upper 11 extending upwardly from sole 13 Said shoe 10 may also include an insole 14, substantially parallel to and substantially proximate and contacting the upper surface 15 of said sole 13. The upper of shoe 10 is enclosed around the foot 40 of a user by laces 18 as shown in FIG. 7. Other available means of enclosing the shoe 10 about foot 40 include straps and buckles, or Velcro® fasteners or other like or similar means without being in limitation of the invention.

The interior surface 12 of the upper 11 further has an instep or medial side 16 and an outstep or lateral side 17.

The ankle brace or wrap 20 may be removably secured around the user's foot 40 as shown in FIGS. 4, 5, 6 and 7. Said brace 20 may be any type commercially available, or comprised of tape, or elastic wrap, or any foot and ankle enclosure or wrap which limits movement of the ankle joint. In practice, the brace may be held in place by straps, laces, tape, elastic wrap or any similar or equivalent means.

Figure 5:
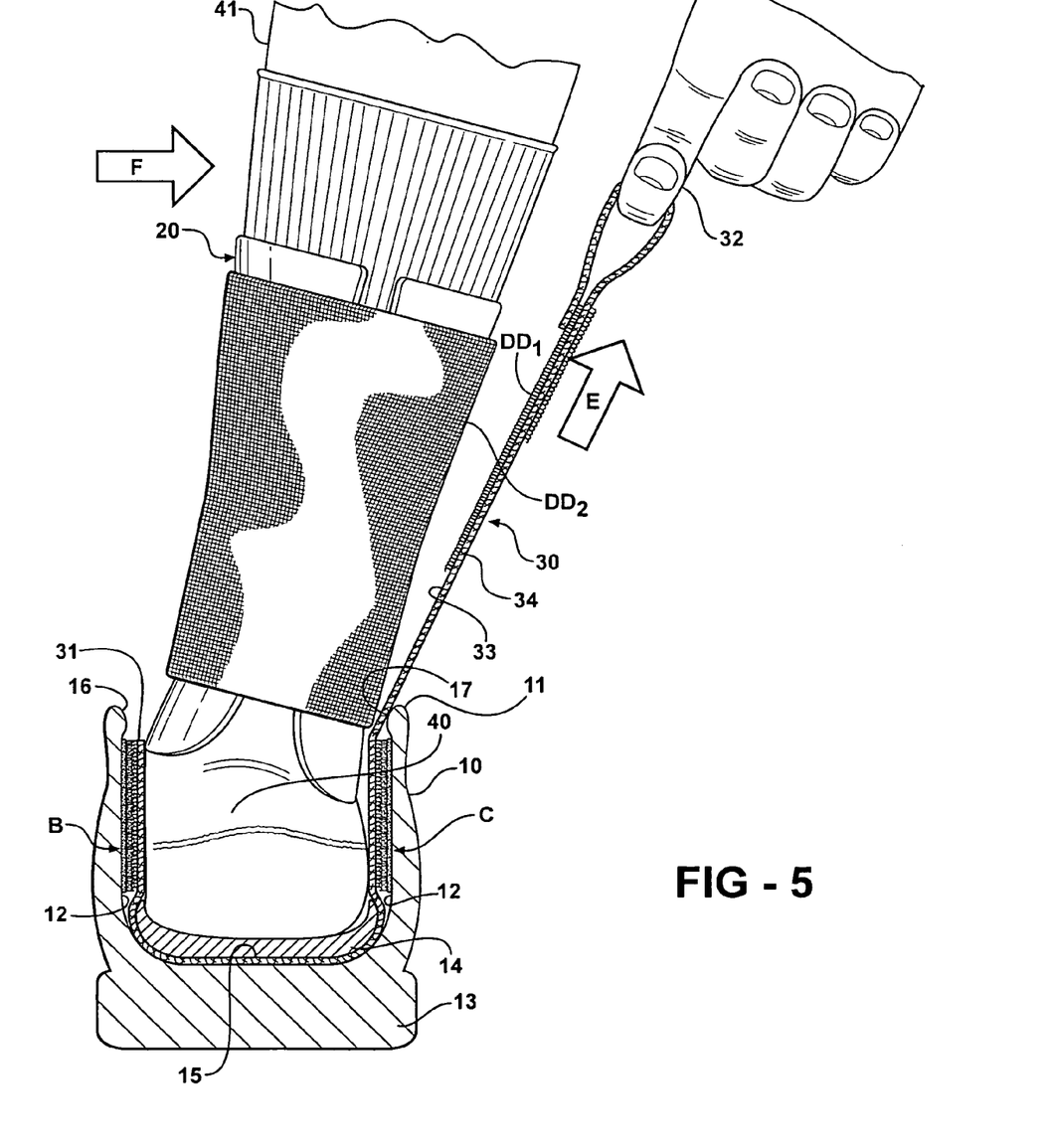
FIG. 5 shows substantially the view of FIG. 4, but additionally demonstrating the method of pulling the strap device taut and affixing the same in taut position at a position on the leg of the user above the shoe.
Figure 6:
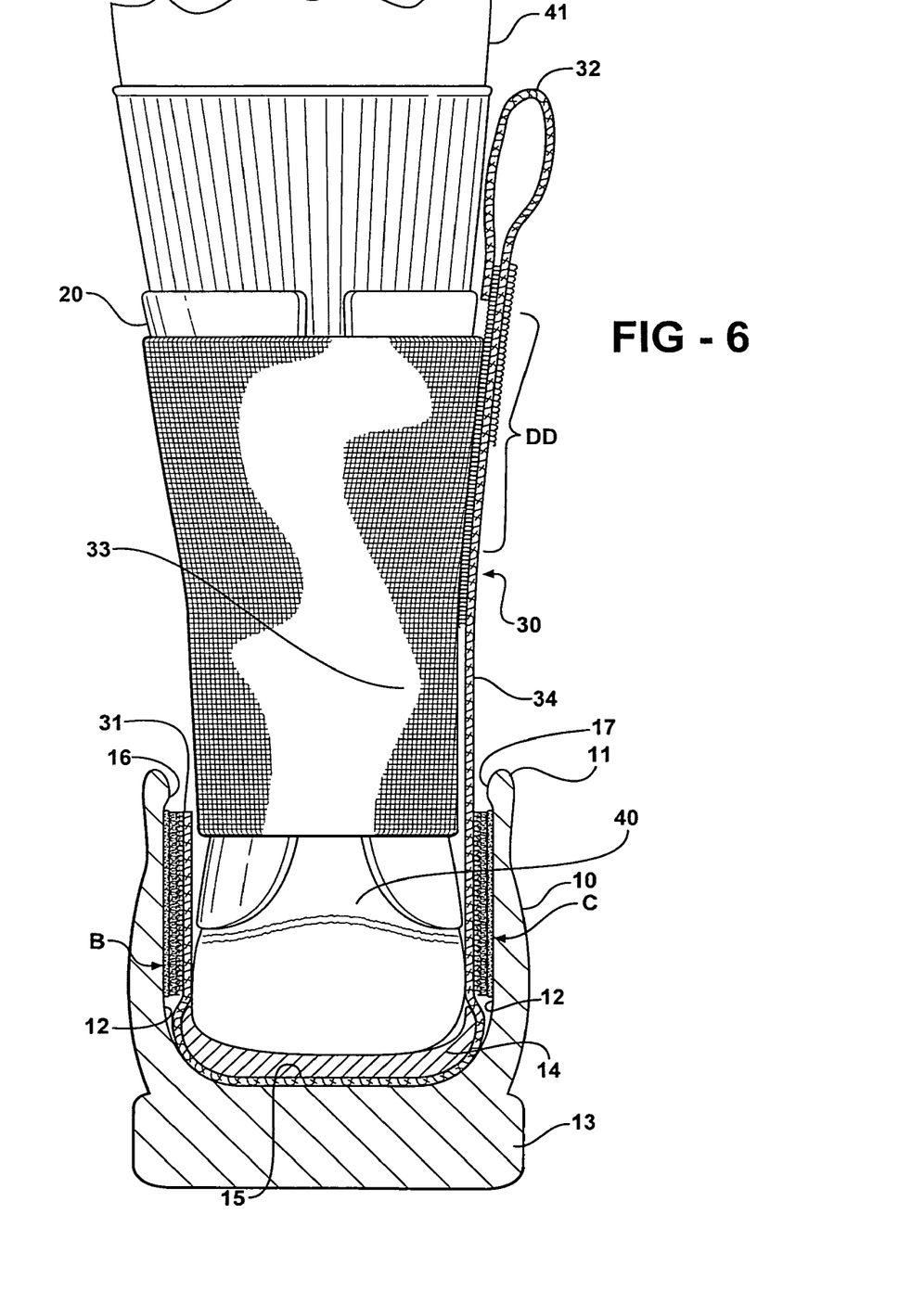
FIG. 6 is a cutaway view of a shoe showing a rear view of a user's right foot and ankle within the shoe, with the strap device held in position by hook and loop fasteners, and affixed to an ankle brace device at a point above the shoe and the user's ankle.

In a featured embodiment of the invention, strap element 30 is attached to the medial side 16 of upper 11 at a first point B on interior surface 12, above the upper surface 15 of sole 13. If an insole 14 is utilized, point B will normally be above said insole 14. Strap 30 then is extended downward proximate medial side 16 until it meets upper surface 15, then extended across upper surface 15 to lateral side 17, then upward proximate to lateral side 17 so that second end 32 extends substantially above upper 11 and the ankle joint of the user. In this embodiment, strap 30 is also attached to the lateral side 17 of upper 11 at second point C on the interior surface 12 above the upper surface of sole 13. If an insole 14 is utilized, point C will normally be above insole 14. Strap 30 extends upwardly along the outstep or medial side 16 substantially on a line which bisects the ankle joint and generally vertical dimension of the user's leg 41 corresponding to the foot 40 inserted within shoe 10. Strap 30 is attached to the medical side 16 and lateral side 17 of interior surface 12 of upper 11 at points B and C, respectively, by corresponding hook and loop fastener elements BB and CC, in the featured embodiment. In practice, strap 30 may also be attached at points B and C by being sewn, glued, snapped or riveted, or by like or similar methods. Said hook and loop fasteners BB and CC may be Velcro®. Strap 30, in the preferred embodiment, also provides a third hook and loop fastener DD, with a first portion DD1 thereof attached to the inner surface 33 of strap 30 at a position proximate and below second end 32, and a second portion DD2 attached to the brace 20 on the outstep or lateral side of leg 41. Strap 30 also has an outer surface 34. A loop feature 35 is provided at second end 32 to facilitate gripping second end 32 as shown in FIG. 5. In practice, as alternatives to hook and loop fastener DD, second end 32 of strap 30 may be attached to brace 20, by straps, laces, elastic wrap, tape or other similar or like means. Second end 32 of strap 30 may also be attached directly to the user's leg 41 by means of adhesive tape or elastic wrap, above brace 20, or if strap 30 is used with a shoe 10, but without a brace 20.

In the featured embodiment, as shown in FIGS. 4, 5, 6 and 7, when the shoe 10 also incorporates an insole 14, strap 30 extends between medial side 16 and lateral side 17 above the upper surface 15 of sole 13 and below the insole 14. (As noted previously, the term instep and medial are utilized interchangeably as are the terms outstep and lateral.)

In practice, strap 30 will be attached at points B and C within the shoe 10. A brace 20, whether a commercial motion limiting ankle brace, tape, or other limiting device will be secured around a user's foot, ankle and lower leg. The foot 40 with brace 30 secured will then be placed within the corresponding shoe 10, so that the strap 30 at point B is proximate to and contacting the instep or medial side of foot 40, with insole 14 between the bottom of foot 40 and sole 13 and point C proximate to and contacting the lateral or outstep side of foot 40. The laces 18, or other securing means of shoe 10, are secured and strap 30 snugly and securely conforms to the outline of user's foot 40 from point B to point C, with second end 32 extending upwardly above the user's ankle and above upper 11 of shoe 10. Second end 32 is gripped by loop 35, or other means, and strap 30 is pulled taut in direction E as demonstrated in FIG. 5. In such taut position, strap 30 is affixed to brace 20 by hook and loop fastener DD. In order to facilitate and maximize the tautness of strap 30 when affixed to brace 20, the user may incline or evert the lower leg 41 corresponding to the enclosed foot 40 in direction F before engaging fastener DD, or equivalent fastening means. Strap 30 may alternatively be pulled taut before the laces 18, or other securing means are secured.

It is a further feature of the invention that, when a shoe 10 and brace 20 are provided or otherwise available, that strap 30 may be provided as a separate kit, further consisting of fasteners BB, CC and DD with portions BB2, CC2 and DD2 being separately attachable to shoe 10 and brace 20 so that strap 30 may be removably and separately utilized with any number of different shoes and/or ankle braces.

Figure 1:
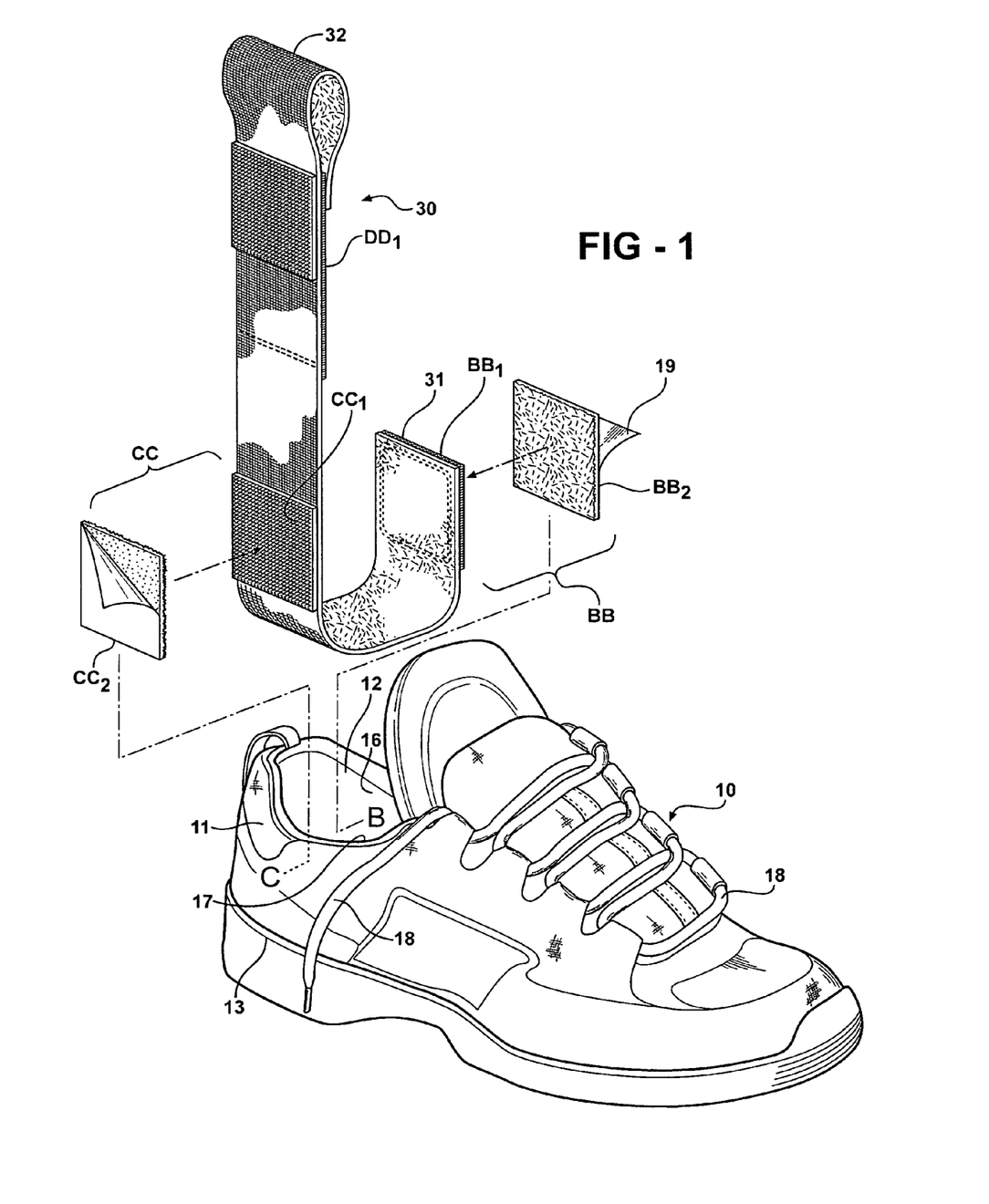
FIG. 1 is an exploded perspective view of a shoe, with the strap device of the present invention, showing the placement and manner of affixation.
Figure 2:
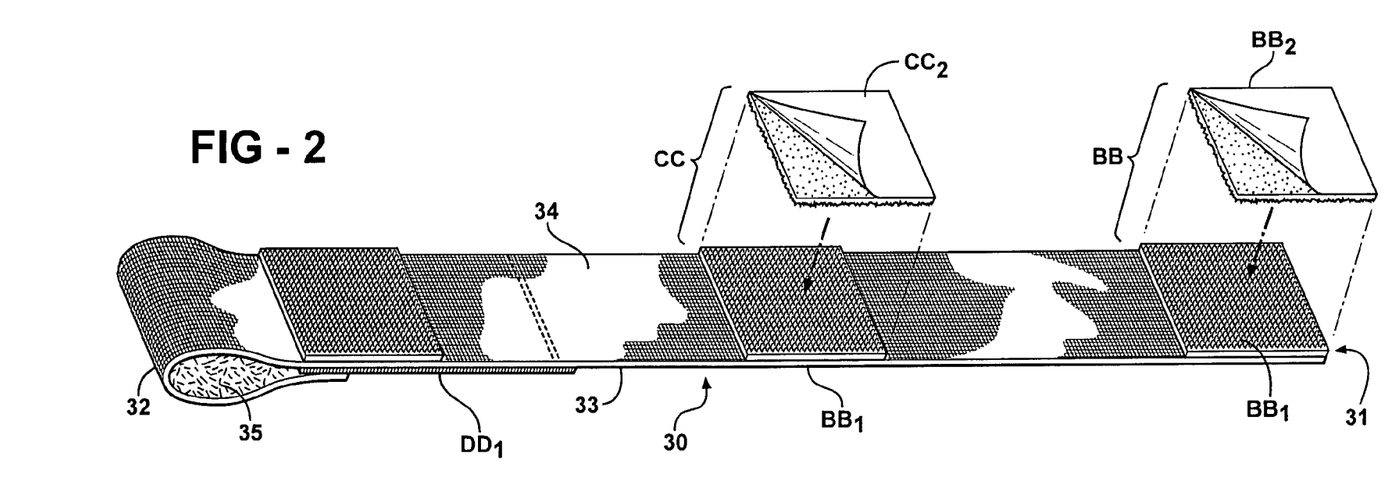
FIG. 2 is a perspective view of the strap of the present invention, together with hook and loop fasteners, from the side thereof which contacts the interior of the upper of the shoe.
Figure 3:
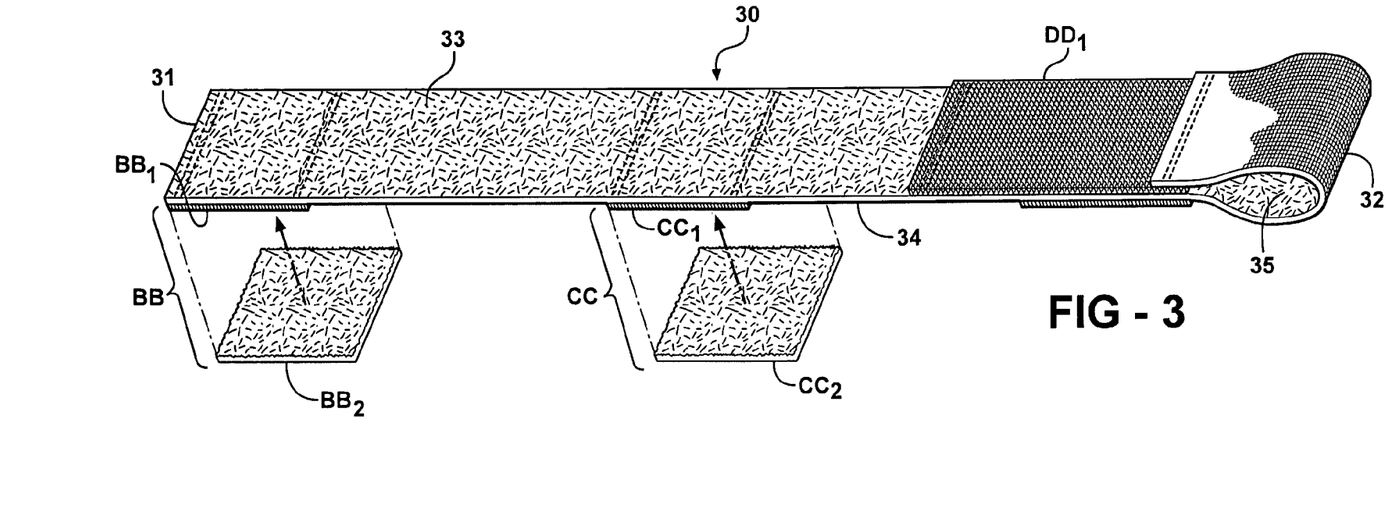
FIG. 3 is a perspective view of the strap device of the present invention, and hook and loop fasteners, from the side opposite that which contacts the interior of the shoe upper.
Figure 4:
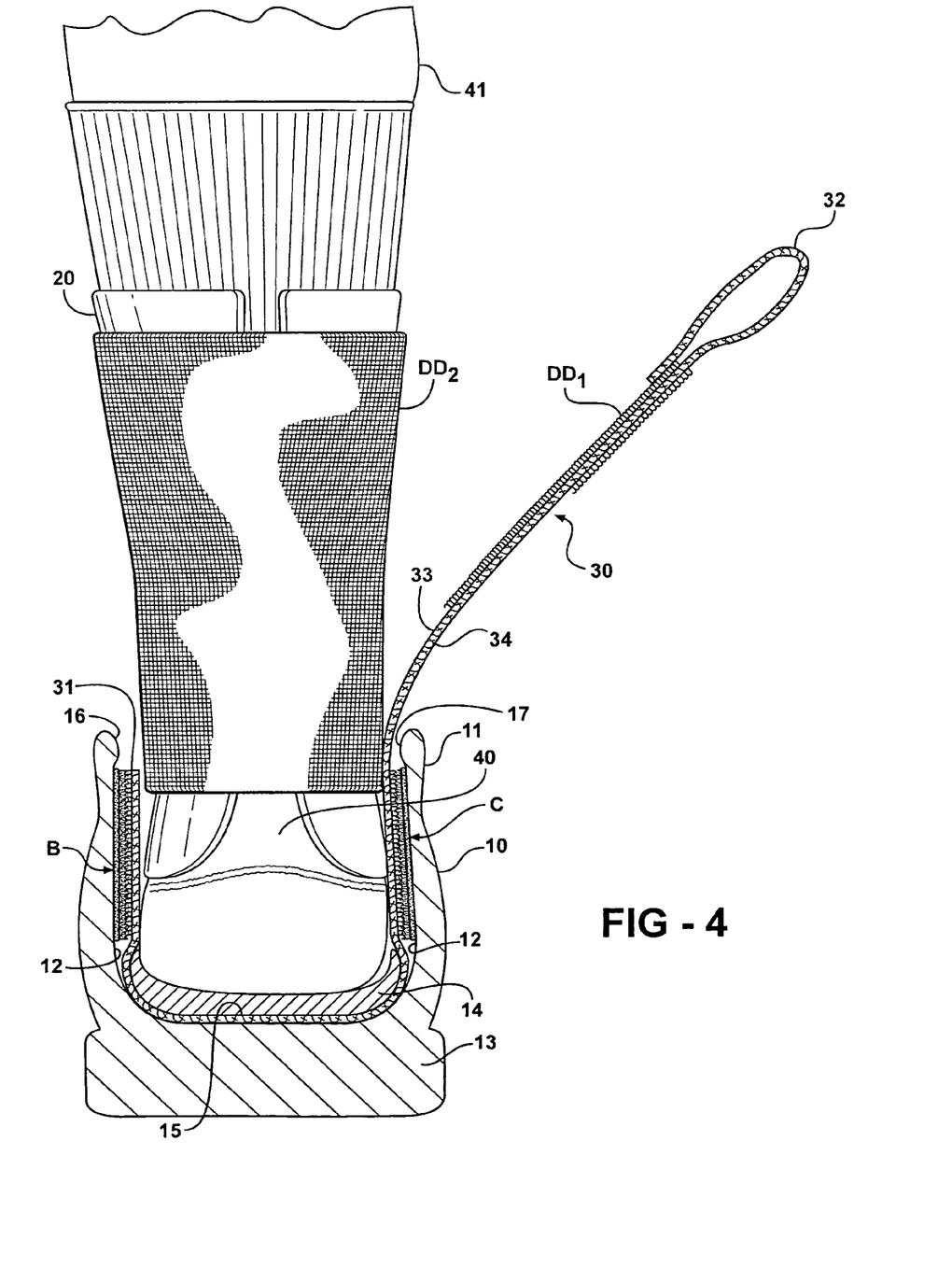
FIG. 4 is a cutaway view of a shoe, showing a rear view of a user's right foot and ankle within the shoe, with the strap device of the current invention affixed by hook and loop fasteners to the interior of the shoe upper, an ankle brace device around the ankle of the user, with the strap running beneath a removable insole of the shoe.

It is further noted that, with regard to hook and loop fasteners, as shown in the featured embodiment, BB, CC and DD, the "hook" and "loop" portions thereof are interchangeable between DD1, DD2; CC1 and CC2; and BB1 and BB2. It is further noted that, as in this feature of the embodiment, when the strap attachment is offered as a kit for utilization with existing shoe(s) and brace(s), that the portions of hook and loop fasteners to be attached within the individual shoes, or to the individual brace, may be a self-adhering element, from which a cover strip 19 may be removed, as shown in FIG. 1, for immediate affixation. In such case, as shown in FIG. 1, the portions of BB2 and CC2 have an adhesive means attached.

Having described my invention, other and additional preferred embodiments will become apparent to those skilled in the art to which it pertains and without deviating from the scope of the appended claims.

What is claimed is:

1. An ankle inversion prevention system comprising:
   a shoe removably fixable around a user's foot, having a sole and upper attached thereto, said upper further comprising an instep side and an outstep side;
   an ankle brace device removably fixable around the user's ankle and lower leg thereabove, the ankle and lower leg corresponding to the foot;
   a unitary strap element extendable beneath the user's foot and upwardly along the user's outer lower leg;
   a first means of attaching said unitary strap element at least one position within the upper of said shoe; and
   a second means of attaching said unitary strap element to said ankle brace device at a position on said outer lower leg.

2. The invention of claim 1, wherein said first means of attaching said unitary strap element is affixed at a first position on the instep side of said upper, extending downward therefrom, passing beneath the user's foot, proximate the sole of said shoe, and then extending upwardly from said sole, and is affixed at a second position on the outstep side of said upper, further extending upwardly therefrom.

3. The invention of claim 2 wherein said shoe further comprises an insole element, substantially parallel to and adjacent above said sole, and said unitary strap element extends between said insole and sole between the first position on said instep side of said upper and the second position on the outstep side of said upper.

4. The invention of claim 1 wherein the first means of attaching said strap is a hook and loop fastening means.

5. The invention of claim 1, wherein said shoe is removably fixable around the user's foot by laces.

6. The invention of claim 1, wherein said shoe is removably fixable around the user's foot by one or more straps.

7. The invention of claim 1, wherein the second means of attaching said unitary strap to said ankle brace device is a hook and loop fastener.

8. The invention of claim 1, wherein the second means of attaching said unitary strap to said ankle brace device is adhesive tape.

9. The invention of claim 1, wherein the second means of attaching said unitary strap to said ankle brace device is an elastic wrap.

10. The invention of claim 1, wherein said unitary strap is drawn taut between attachment at least one position within the upper and attachment to the ankle brace device.

11. The invention of claim 1, wherein said shoe is an athletic shoe.

12. A method of preventing ankle inversion, comprising the following steps:
- A. Providing a shoe removably fixable about a user's foot, said shoe further comprising a sole and upper attached thereto, and said upper further comprising an instep side and an outstep side;
- B. Providing an ankle brace device removably fixable around user's ankle and lower leg thereabove, the ankle and lower leg corresponding to the foot;
- C. Providing a unitary strap element having a first end and attached at least one position within the upper of said shoe, extending across the sole of said shoe, and a second end extending upwardly from within the outstep side of the upper of said shoe to a position above said upper;
- D. Affixing the ankle brace device about the user's ankle and lower leg;
- E. Inserting said user's foot corresponding to the ankle and leg within said shoe, such that the strap element runs between the user's foot and the sole and upper of said shoe between the instep side and outstep side of said upper and extends above said upper on said outstep side;
- F. Affixing the shoe about the user's foot; and
- G. Exerting upward pressure on the second end of said strap and affixing the same to a position on the ankle brace device above the shoe upper.

13. The method of claim 12, wherein steps F and G are reversed.

14. The method of claim 12, wherein said unitary strap element of step C is attached at a first position on the instep side of the upper of the shoe of step A, extending downwardly therefrom, then extending horizontally proximate the sole of said shoe, then extending upwardly from said sole and affixed at a second position on the outstep side of said upper, further extending upwardly therefrom.

15. The method of claim 14, wherein the shoe of step A further comprises an insole element substantially parallel and adjacent above said sole, and said unitary strap element of step C extends between said insole and sole between said first position on the instep side of said upper and second position on the outstep side of said upper.

16. The method of claim 14, wherein the strap element of step C is affixed within the upper of the shoe of Claim A by hook and loop fasteners.

17. The method of claim 12, wherein step F is accomplished by means of laces.

18. The method of claim 12, wherein step F is accomplished by one or more straps.

19. The method of claim 12, wherein said strap is affixed to said ankle brace device in step G by hook and loop fastener.

20. The method of claim 12, wherein strap is affixed to said ankle brace in step G by adhesive tape.

21. The method of claim 12, wherein said strap is affixed to said ankle brace in step G by an elastic wrap.

22. The method of claim 11, wherein the shoe of step A is an athletic shoe.

* * * * *